United States Patent
Chern et al.

(10) Patent No.: US 8,969,361 B2
(45) Date of Patent: Mar. 3, 2015

(54) CYCLOPROPANECARBOXYLATE ESTERS OF PURINE ANALOGUES

(71) Applicant: Annji Pharmaceutical Co., Ltd., Taipei (TW)

(72) Inventors: Ji-Wang Chern, Taipei (TW); Shin-Yu Lai, Taipei (TW); Pei-Teh Chang, Taipei (TW)

(73) Assignee: Annji Pharmaceutical Co., Ltd., Taipei (TW)

( * ) Notice: Subject to any disclaimer, the term of this patent is extended or adjusted under 35 U.S.C. 154(b) by 0 days.

(21) Appl. No.: 13/855,692

(22) Filed: Apr. 2, 2013

(65) Prior Publication Data

US 2013/0281517 A1 Oct. 24, 2013

Related U.S. Application Data

(60) Provisional application No. 61/635,931, filed on Apr. 20, 2012.

(51) Int. Cl.

| | |
|---|---|
| *A01N 43/90* | (2006.01) |
| *A61K 31/522* | (2006.01) |
| *C07D 209/34* | (2006.01) |
| *C07D 403/06* | (2006.01) |
| *C07D 401/06* | (2006.01) |
| *C07D 401/14* | (2006.01) |
| *C07D 409/06* | (2006.01) |
| *C07D 405/06* | (2006.01) |
| *C07D 403/14* | (2006.01) |
| *A61K 38/45* | (2006.01) |
| *C07D 473/32* | (2006.01) |

(52) U.S. Cl.
CPC ............ *C07D 209/34* (2013.01); *C07D 403/06* (2013.01); *C07D 401/06* (2013.01); *C07D 401/14* (2013.01); *C07D 409/06* (2013.01); *C07D 405/06* (2013.01); *C07D 403/14* (2013.01); *A61K 31/522* (2013.01); *A61K 38/45* (2013.01); *C07D 473/32* (2013.01)
USPC ..................................... 514/263.37; 544/265

(58) Field of Classification Search
CPC ........................... C07D 473/18; A61K 31/522
USPC ........................... 544/265; 514/263.7, 263.37
See application file for complete search history.

(56) References Cited

U.S. PATENT DOCUMENTS

| 4,162,328 A | 7/1979 | Zurfluh |
|---|---|---|
| 7,846,793 B2 | 12/2010 | Olsen et al. |

FOREIGN PATENT DOCUMENTS

WO    WO 2009111739 A2 * 9/2009

OTHER PUBLICATIONS

N. Kunou et al., 68 Journal of Controlled Release 68 263-271 (2000).*
G. M Cleator et al., The Herpesviridae in, Principles and Practice of Clinical Virology 23-26, 25 (Arie J. Zuckerman et al., eds., 5th ed., 2004) ("Cleator").*
E. Gershburg et al., 56 Journal of Antimicrobial Chemotherapy, 277-281, 277 (2005).*
C. Mathéet al., 71 Antiviral Research, 276-281 (2006).*
B Testa et al., Prodrug Design in, 5 Encyclopedia of Pharmaceutical Technology, 3008-3014 (J. Swarbrick ed., 3rd ed., 2007).*
C. McGuigan et al., 18 Bioorganic & Medicinal Chemistry Letters, 4364-4367 (2008).*
M. Derudas et al., 52 Journal of Medicinal Chemistry, 5520-5530 (2009).*
P. Raju et al., 94 Helvetica Chimica Acta, 592-596 (2011).*
J.H. Poupaert, Drug Design: Basic Principles and Applications, in 2 Encyclopedia of Pharmaceutical Technology 1362-1369, 1367 (James Swarbrick ed., 3rd ed., 2007).*
R. Wilson et al., 71 Journal of Organic Chemistry 8329-8351, 8326 (2006).*
N.G. Anderson, Practical Process & Research Development 27-50 (2000).*
N. Anderson, 8 Organic Process Research & Development 260-265 (2004).*
H.-J. Federsel, 12 Organic Process Research & Development 512-521 (2008).*
Majumdar S.; Nashed Y. E.; Patel K.; Jain R.; Itahashi M.; Neumann DM.; Hill J. M.; Mitre A. K. (2005) Dipeptide monoester ganciclovir prodrugs for treating HSV-1-induced corneal epithelial and stromal keratitis: in vitro and in vivo evaluations. J Ocul Pharmacol Ther, Dec;21(6):463-74. (Abstract only).

* cited by examiner

*Primary Examiner* — Alexander R Pagano
(74) *Attorney, Agent, or Firm* — Hsiu-Ming Saunders; Intellectual Property Connections, Inc.

(57) ABSTRACT

Cyclopropanecarboxylate esters of purine analogues, method of making and using the same for treating herpes virus infections and tumors are disclosed.

18 Claims, 1 Drawing Sheet

CYCLOPROPANECARBOXYLATE ESTERS OF PURINE ANALOGUES

REFERENCE TO RELATED APPLICATION

The present application claims the priority to U.S. Provisional Application Ser. No. 61/635,931, filed Apr. 20, 2012, which is herein incorporated by reference in its entirety.

FIELD OF THE INVENTION

The present invention relates generally to ganciclovir cyclopropanecarboxylate ester derivatives and intermediates, preparation and the use thereof.

BACKGROUND OF THE INVENTION

U.S. Pat. No. 4,162,328 discloses cyclopropane carboxylic acid esters for use as pesticides. U.S. Pat. No. 7,846,937 discloses cyclopropanecarboxylate esters of acyclovir. Majumdar et al disclose dipeptide monoester ganciclovir (GCV) prodrugs, of which Val-Val-GCV demonstrates excellent corneal permeability and chemical stability, high aqueous solubility, and substantial in vivo antiviral activity against the herpes simplex virus type 1 (HSV-1) (Ocul Pharmacol Ther. 2005; 21 (6):463-74).

SUMMARY OF THE INVENTION

In one aspect, the invention relates to a compound having the structure

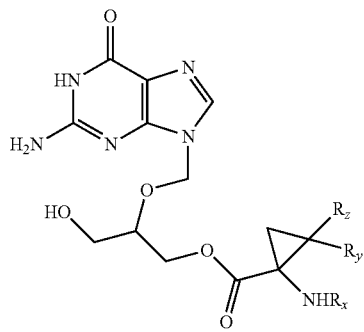

Formula (T)

or a pharmaceutically acceptable salt, a solvate or hydrate, a prodrug, or a metabolite thereof,
wherein
$R_x$, and $R_z$, are each independently hydrogen or ($C_1$-$C_6$) alkyl; and
$R_y$ is hydrogen, ($C_1$-$C_6$)alkyl, halo($C_1$-$C_6$)alkyl, ($C_6$-$C_{18}$) aryl, halo($C_6$-$C_{18}$)aryl, or ($C_3$-$C_{18}$)heteroaryl.

In one embodiment of the invention, wherein $R_x$ and $R_z$ are each independently hydrogen or methyl; and $R_y$ is hydrogen, methyl, trifluoromethyl, phenyl, 4-bromophenyl, 2-furyl, or 2-pyridyl.

In another embodiment of the invention, wherein $R_x$ and $R_z$ are each independently hydrogen; and $R_y$ is hydrogen, methyl, trifluoromethyl, phenyl, 4-bromophenyl, 2-furyl, or 2-pyridyl.

In another embodiment of the invention, wherein $R_x$ is methyl; and $R_y$ and $R_z$ are each independently hydrogen.

In another embodiment of the invention, wherein $R_x$ is hydrogen; and $R_y$, and $R_z$ are each independently methyl.

In another embodiment of the invention, wherein the compound is selected from the group consisting of 1-amino-cyclopropanecarboxylic acid 2-(2-amino-6-oxo-1,6-dihydro-purin-9-yl methoxy)-3-hydroxypropyl ester, 1-amino-2-(4-bromo-phenyl)-cyclopropanecarboxylic acid 2-(2-amino-6-oxo-1,6-dihydro-purin-9-ylmethoxy)-3-hydroxypropyl ester, 1-amino-2-phenyl-cyclopropanecarboxylic acid 2-(2-amino-6-oxo-1,6-dihydro-purin-9-ylmethoxy)-3-hydroxypropyl ester, 1-amino-2-methyl-cyclopropanecarboxylic acid 2-(2-amino-6-oxo-1,6-dihydro-purin-9-ylmethoxy)-3-hydroxypropyl ester, 1-amino-2-trifluoromethyl-cyclopropanecarboxylic acid 2-(2-amino-6-oxo-1,6-dihydro-purin-9-ylmethoxy)-3-hydroxypropyl ester, 1-amino-2-furan-2-yl-cyclopropanecarboxylic acid 2-(2-amino-6-oxo-1,6-dihydro-purin-9-ylmethoxy)-3-hydroxypropyl ester, and 1-amino-2-pyridin-2-yl-cyclopropanecarboxylic acid 2-(2-amino-6-oxo-6-dihydro-purin-9-yl-methoxy)-3-hydroxypropyl ester.

In another embodiment of the invention the compound is 1-methylamino-cyclopropanecarboxylic acid 2-(2-amino-6-oxo-1,6-dihydro-purin-9-ylmethoxy)-3-hydroxypropyl ester.

In another embodiment of the invention, the compound is 1-amino-2,2-dimethyl-cyclopropanecarboxylic acid 2-(2-amino-6-oxo-1,6-dihydro-purin-9-ylmethoxy)-3-hydroxypropyl ester.

In another aspect, the invention relates to a composition comprising a compound as aforementioned, or a pharmaceutically acceptable salt, a solvate or hydrate, a prodrug, or a metabolite thereof, and a pharmaceutically acceptable carrier or vehicle.

Further in another aspect, the invention relates to a method for preparing a compound as claimed in claim 1, comprising:
(1) reacting a compound of Formula (W)

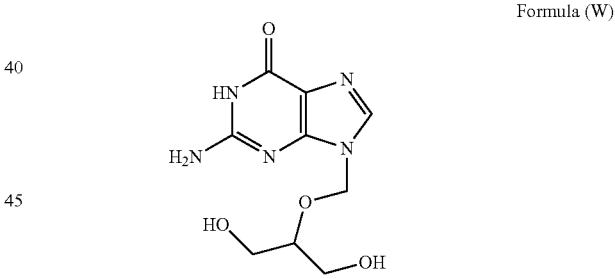

Formula (W)

with a mixture of dimethylforamide/dimethylacetamide to afford a compound of Formula (X)

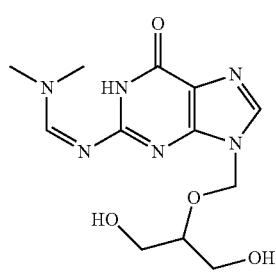

Formula (X)

(2) reacting the compound of Formula (X) with a compound of Formula (Y)

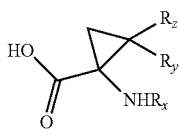

Formula (Y)

wherein $R_x$ and $R_z$ are each independently hydrogen or ($C_1$-$C_6$)alkyl; and $R_y$ is hydrogen, ($C_1$-$C_6$)alkyl, halo($C_1$-$C_6$)alkyl, ($C_6$-$C_{18}$)aryl, halo($C_6$-$C_{18}$)aryl, or ($C_3$-$C_{18}$)heteroaryl to afford a compound of Formula (Z)

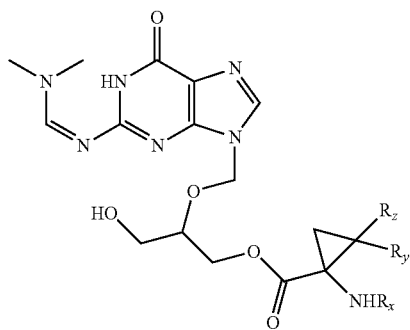

Formula (Z)

wherein: $R_x$ and $R_z$ are each independently hydrogen or ($C_1$-$C_6$)alkyl; and $R_y$ is hydrogen, ($C_1$-$C_6$)alkyl, halo($C_1$-$C_6$)alkyl, ($C_6$-$C_{18}$)aryl, halo($C_6$-$C_{18}$)aryl, or ($C_3$-$C_{18}$)heteroaryl; and (3) reacting the compound of Formula (Z) with methanol and trifluoroacetic acid to afford the compound of Formula (T), wherein: $R_x$ and $R_z$ are each independently hydrogen or ($C_1$-$C_6$)alkyl; and $R_y$ is hydrogen, ($C_1$-$C_6$)alkyl, halo($C_1$-$C_6$)alkyl, ($C_6$-$C_{18}$)aryl, halo($C_6$-$C_{18}$)aryl, or ($C_3$-$C_{18}$)heteroaryl.

Further in another aspect, the invention relates to a compound or a pharmaceutically acceptable salt, a solvate or hydrate, a prodrug, or a metabolite thereof as aforementioned, for use as an anti-herpes agent for treating herpes virus infection. The herpes virus infection may be herpes simplex virus infection, herpes zoster infection, or cytomegalovirus infection.

Further in another aspect, the invention relates to a compound or a pharmaceutically acceptable salt, a solvate or hydrate, a prodrug, or a metabolite thereof as aforementioned, for use as an anti-tumor agent for inhibiting tumor growth.

In another embodiment of the invention, the compound of the invention may be used for treating cancer. A cancer patient may be first administered a vector, such as an adenovector, comprising a DNA insert encoding HSV thymidine kinase, said vector expressing HSV thymidine kinase in the tumor cells of the subject, followed by administration of the compound of the invention.

Yet in another aspect, the invention relates to use of a compound or a pharmaceutically acceptable salt, a solvate or hydrate, a prodrug, or a metabolite thereof as aforementioned in the manufacture of a medicament for treating herpes virus infection. The medicament may be for treating herpes simplex virus infection, herpes zoster infection, or cytomegalovirus infection.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

Figure 1:
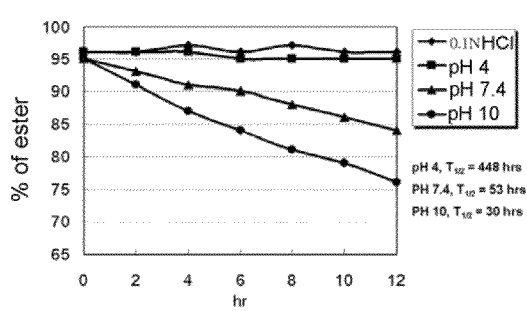
FIG. 1 shows aqueous stability of Compound 3 in buffer solutions of various pH values at 40° C.

It is to be understood that this invention is not limited to particular variations set forth and may vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Unless otherwise indicated, the words and phrases presented in this document have their ordinary meanings to one of skill in the art. The following explanations of certain terms are meant to be illustrative rather than exhaustive. These terms have their ordinary meanings given by usage in the art and in addition include the following explanations.

The term "about" refers to a variation of 10 percent of the value specified; for example about 50 percent carries a variation from 45 to 55 percent.

The term "and/or" refers to any one of the items, any combination of the items, or all of the items with which this term is associated.

The singular forms "a," "an," and "the" include plural reference unless the context clearly dictates otherwise.

Specific and preferred values listed below for radicals, substituents, and ranges, are for illustration only; they do not exclude other defined values or other values within defined ranges for the radicals and substituents.

A dash ("-") that is not between two letters or symbols is used to indicate a point of attachment for a moiety or substituent. For example, the moiety —CONH$_2$ is attached through the carbon atom.

The term "amino" refers to —NH$_2$. The amino group can be optionally substituted as defined herein for the term "substituted."

The term "alkyl" refers to a $C_1$-$C_{18}$ hydrocarbon containing normal, secondary, tertiary or cyclic carbon atoms. Examples are methyl, ethyl, 1-propyl, 2-propyl, 1-butyl, 2-methyl-1-propyl (iso-butyl, —CH$_2$CH(CH$_3$)$_2$), 2-butyl (sec-butyl, —CH(CH$_3$)CH$_2$CH$_3$), 2-methyl-2-propyl (tert-butyl, —C(CH$_3$)$_3$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl.

The alkyl can be a monovalent hydrocarbon radical, as described and exemplified above, or it can be a divalent hydrocarbon radical (i.e., alkylene).

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The phrase "compounds of the disclosure" refer to compounds of Formula (T) and pharmaceutically acceptable enantiomers, diastereomers, and salts thereof. Similarly, references to intermediates, are meant to embrace their salts where the context so permits.

The terms "halogen" or "halo" refer to fluoro, chloro, bromo, and iodo. Similarly, the term "halogen" refers to fluorine, chlorine, bromine, and iodine.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene.

Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl, or hydroxy.

The term "hydrate" refers to the complex where the solvent molecule is water.

The term "metabolite" refers to any compound of the Formula (T) produced in vivo or in vitro from the parent drug, or its prodrugs.

The term "pharmaceutically acceptable salts" refers to ionic compounds, wherein a parent non-ionic compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids. Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can form pharmaceutically acceptable salts with various amino acids. For a review on pharmaceutically acceptable salts, see, e.g., Berge et al., *J. Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in Remington: The Science and Practice of Pharmacy, $21^{st}$ edition, Lippincott, Williams & Wilkins, (2005).

The term "pharmaceutically effective amount" refers to any amount of the composition for the topical prevention and treatment of herpes simplex virus infections in humans that is effective in treating the Herpes virus infection by killing or inhibiting the growth of the Herpes virus, causing the Herpes virus to lose pathogenicity, or any combination thereof.

The term "prodrug" refers to any pharmaceutically acceptable form of compound of the Formula (T), which, upon administration to a patient, provides a compound of the Formula (T). Pharmaceutically acceptable prodrugs refer to a compound that is metabolized, for example hydrolyzed or oxidized, in the host to form a compound of the Formula (T). Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The prodrug can be readily prepared from the compounds of Formula (T) using methods known in the art. See, e.g. See Notari, R. E., "Theory and Practice of Prodrug Kinetics," *Methods in Enzymology*, 112:309 323 (1985); Bodor, N. "Novel Approaches in Prodrug Design," *Drugs of the Future*, 6(3):165 182 (1981); and Bundgaard, H., "Design of Prodrugs: Bioreversible-Derivatives for Various Functional Groups and Chemical Entities." in "Design of Prodrugs" (H. Bundgaard, ed.), Elsevier, N.Y. (1985); Burger's Medicinal Chemistry and Drug Chemistry, Fifth Ed., Vol. 1, pp. 172 178, 949 982 (1995).

The term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

The compound of the invention may be administered by any route appropriate to the condition to be treated, which includes but not limited to oral, inhalation, subcutaneously, intramuscularly, intravenously, transdermally, ocularly, intranasally, rectally, topically, sublingually, buccally, and so on. Oral or topical administration is generally preferred for treatment of a herpes virus infection described herein. Ocular administration is proffered for the treatment of herpes simplex virus infected keratitis.

The invention relates to cyclopropanecarboxylate esters of ganciclovir, which exhibit an unexpected stability to an acidic or basic condition. For example, Compound 3 exhibits a longer half-life (i.e., stability) as compared to valganciclovir [Dimitrois er al, *Drug. Dev. Ind. Pharm.* 31, 879-894 (2005)] when incubated in an aqueous solution of pH 1, 4, 7.4 or 10 (FIG. 1). This unexpected aqueous stability is beneficial when making a pharmaceutical formulation having an aqueous vehicle such as an ophthalmic solution or ointment.

Methods of Making the Compounds of Formula (T).

The compounds described herein can be prepared by any of the applicable techniques of organic synthesis. Many such techniques are well known in the art. However, many of the known techniques are elaborated in "Compendium of Organic Synthetic Methods" (John Wiley & Sons. New York) Vol. 1, Ian T. Harrison and Shuyen Harrison (1971); Vol. 2, Ian T. Harrison and Shuyen Harrison (1974); Vol. 3. Louis S. Hegedus and Leroy Wade (1977); Vol. 4. Leroy G. Wade Jr., (1980); Vol. 5, Leroy G. Wade Jr. (1984); and Vol. 6, Michael B. Smith; as well as March, J., "Advanced Organic Chemistry", 3rd Edition, John Wiley & Sons, New York (1985); "Comprehensive Organic Synthesis. Selectivity, Strategy & Efficiency in Modern Organic Chemistry, In 9 Volumes", Barry M. Trost, Editor-in-Chief, Pergamon Press, New York (1993); "Advanced Organic Chemistry, Part B: Reactions and Synthesis", 4th Ed.; Carey and Sundberg; Kluwer Academic/Plenum Publishers: New York (2001); "Advanced Organic Chemistry, Reactions, Mechanisms, and Structure", 2nd Edition, March, McGraw Hill (1977); "Protecting Groups in Organic Synthesis", 2nd Edition, Greene, T. W., and Wutz, P. G. M., John Wiley & Sons, New York (1991); Katritzky, A. R. "Handbook of Heterocyclic Chemistry", Pergamon Press Ltd; New York (1985), Katritzky, A. R. "Comprehensive Heterocyclic Chemistry", Volumes 1-8 Pergamon Press Ltd; New York (1984), and "Comprehensive Organic Transformations", 2nd Edition, Larock. R. C., John Wiley & Sons, New York (1999). Exemplary methods of making the compounds described herein are described herein in the examples below.

Numerous modifications and variations of the presently disclosed subject matter are possible in light of the above teachings. Specific ranges, values, and embodiments provided herein are for illustration purposes only and do not otherwise limit the scope of the disclosed subject matter, as defined by the claims. The starting materials useful to synthesize the compounds of the present disclosure are known to those skilled in the art and can be readily manufactured or are commercially available. The following methods set forth below are provided for illustrative purposes and are not intended to limit the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Generally, a compound of formula T may be prepared from a compound of formula II where Pg and $Pg^1$ represent suitable amine protecting groups (Scheme 1).

A compound of Formula II is reacted with a suitable reagent for removing the protecting groups without adversely affecting the compound of Formula I. The condition used to remove a protecting group depends on the chemical nature of the protecting group and other functional groups of the compound, and are within the knowledge of skilled artisan. For example, a compound of formula II, where Pg is t-butyloxy-carbonyl. $Pg^1$ is N'N'-dimethylformyl, is reacted with an acid such as trifluoro acetic acid in a suitable solvent such as methylene dichloride to afford a compound of formula I.

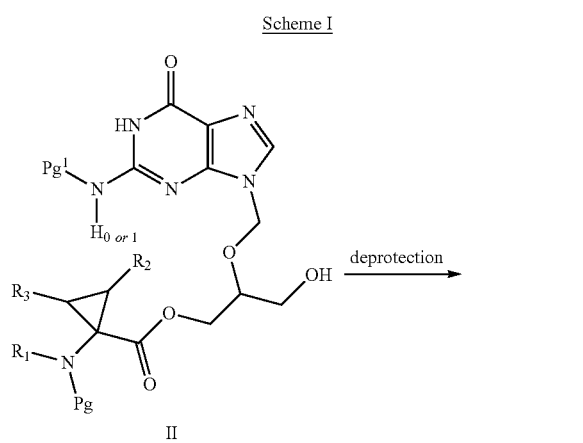

Generally, a compound of formula II where Pg is an amino protecting group may be prepared from protected ganciclovir and a compound of formula III, where Pg represents a suitable amino protecting group such as t-butyloxy-carbonyl group (Scheme II).

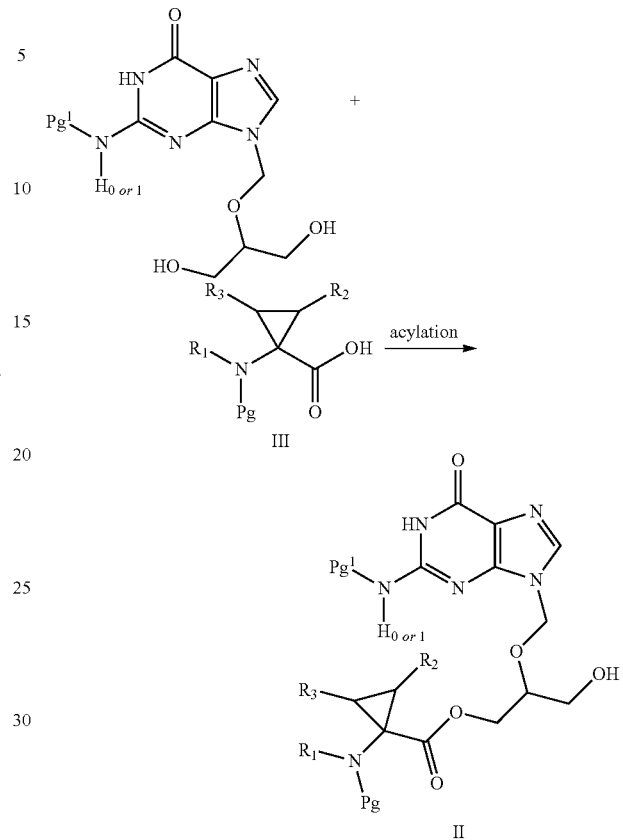

Protected ganciclovir is combined with a compound of formula III under an acylation reaction condition. Acylation reactions to transfer a compound of formula III encompass an ester formation reaction similar to those are conventionally used in the art and synthetic methods used therein can also be applied. For example, well known coupling reagents such as carbodiimides with or without the use of well known additives such as dimethylaminopyridine, 1-hydroxybenzotriazole, etc. may be used to facilitate esterification. For example, well known acylation reagents such as oxalyl chloride, thionyl chloride with or without dimethylformamide may be used to activate a compound of Formula III. The reaction may also be performed in the presence of a base such as triethylamine, pyridine and so on. The reaction is carried out in an aprotic solvent such as methylene dichloride, chloroform, 1,2-dichloroethane, acetonitrile, dimethylformamide, tetrahydrofuran, dioxane, pyridine and the like.

Generally, a compound of protected ganciclovir where $Pg^1$ is an amino protecting group may be prepared from ganciclovir and a suitable amino protecting group (Scheme III).

Ganciclovir is combined with a protection reagent under a suitable condition depending on reagent solubility and chemical nature. For example, well known amino, hydroxyl protection reagent such as trimethylsilyl chloride, t-butyldimethylsilyl chloride, and triphenylmethyl chloride can be used as an amino or hydroxyl protecting group of ganciclovir. For example, well known amino protection reagent such as dimethylamine dimethyl acetal, dimethylamine diethyl acetal, dimethylamine diphenyl acetal can be served as an amino protecting group of ganciclovir. The reaction may also be performed in the presence of a base such as triethylamine, pyridine etc. The protection reaction when amino hydroxyl protecting reagent is used is carried out in an aprotic solvent such as methylene dichloride, chloroform, 1,2-dichloroethane, acetonitrile, dimethylformamide, tetrahydrofuran, dioxane, pyridine etc. The protection reaction when dimethylamine dialky acetal is used is carried out in a protic solvent such as methanol, ethanol etc. under a reflux condition.

Scheme III

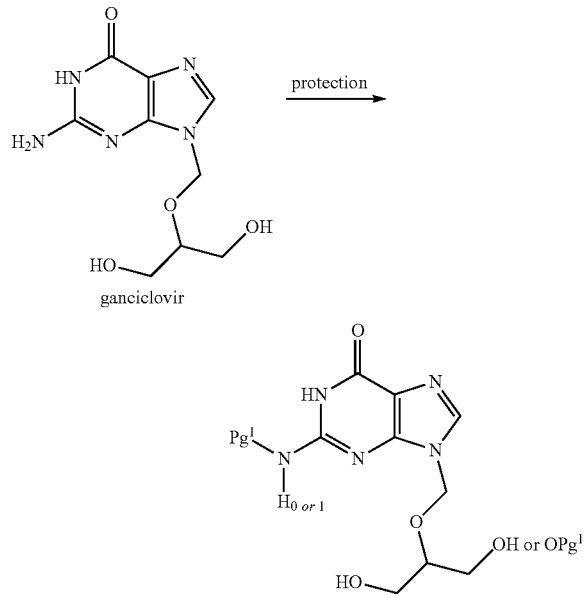

ganciclovir

Example 1

Preparation of N'-[9-(2-Hydroxy-1-hydroxymethyl-ethoxymethyl)-6-oxo-6,9-dihydro-1H-purin-2-yl]-N, N-dimethyl-formamidine (Compound 1)

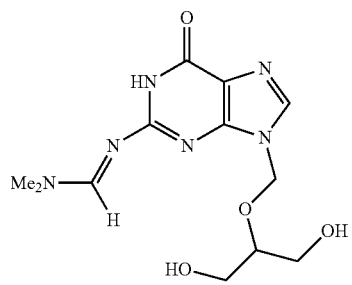 [SMILES: CN(C)/C=N/c1nc2c(ncn2COC(CO)CO)c(=O)[nH]1]

A mixture of gancyclovir (2.04 g; 8 mmol) and DMF-DMA (6 ml) in 75 ml MeOH was heated to reflux for 10 hr. The organic solvent was evaporated by vacuum. Residue solid was recrystallized by MeOH to yield 2.135 g (86%) of compound 1 as a white crystal; mp: 226-227° C. $^1$H NMR (DMSO-d$_6$, 400 MHz) δ 3.12 (s, 3H), 3.02 (s, 3H), 3.29-3.35 (m, 5H), 3.41-3.46 (m, 2H), 3.58-3.64 (m, 1H), 4.60 (t, J=5.6, 2H), 5.51 (s, 2H), 7.91 (s, 1H), 8.55 (s, 1H), 11.30 (s, 1H). $^{13}$C NMR δ 158.0, 157.6, 157.4, 150.0, 138.6, 119.3, 80.3, 71.4, 60.8, 40.7, 34.6. ESI-MS: m/z 311.1 [M+H]$^+$.

Example 2

Preparation of 1-tert-Butoxycarbonylamino-cyclopropanecarboxylic acid 2-[2-(dimethylamino-methyleneamino)-6-oxo-1,6-dihydro-purin-9-ylmethoxy]-3-hydroxypropyl ester (Compound 2)

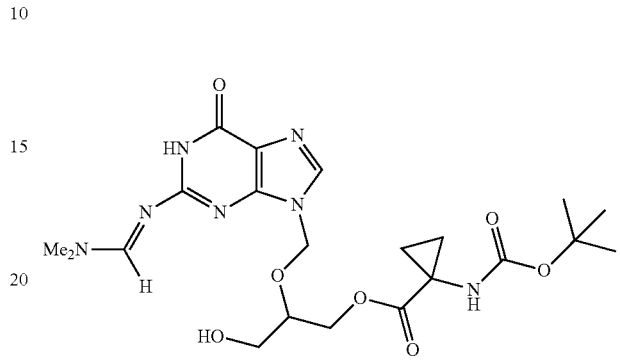

A suspension of compound 1 (2.13 g; 6.9 mmol) and EDC (1.98 g; 10.3 mmol) in 80 ml dry pyridine was added with a solution of N-Boc-cyclopropylamin carboxylic acid 1.52 g (7.57 mmol) and dimethyl aminopyridine 85 mg (0.7 mmol) in 20 ml dry pyridine by portions at room temperature during 48 h. The suspension was filtered and filtrate evaporated by vacuum and purified by column chromatography (silica gel 3.5×12 cm with eluent MeOH/CHCl$_3$=1/19) to afford compound 2 (1.5 g, 44%) as liquid. $^1$H NMR (CD$_3$OD, 400 MHz) δ0.59 (s, 3H), 2.78 (s, 3H), 2.41 (s, 3H), 2.44-2.54 (m, 4H), 2.72-2.81 (m, 21H), 3.16 (t, J=4 Hz, 1H), 3.28 (dd, J=12.8 Hz, J=5.6 Hz, 1H), 3.44 (dd, J=12 Hz, J=3.6 Hz, 1H), 4.80 (s, 2H), 7.13 (s, 1H), 7.84 (s, 1H), $^{13}$C NMR δ 18.3, 28.7, 34.8, 35.4, 41.6, 49.6, 62.3, 65.1, 72.9, 78.3, 80.5, 120.1, 140.6, 152.2, 158.5, 159.3, 160.0, 160.1, 174.4. ESI-MS: m/z 494.2 [M+H]$^+$. HRMS (ESI) cald for C21H32N7O7 [M+H]$^+$ m/z, 494.2363. found 494.2378.

Example 3

1-amino-cyclopropanecarboxylic acid 2-(2-amino-6-oxo-1,6-dihydro-purin-9-yl methoxy)-3-hydroxypropyl ester (Compound 3)

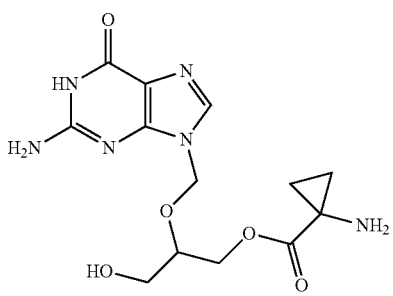

A solution of compound 2 (1.5 g; 3.0 mmol) in MeOH (30 ml) was added TFA (2 ml) at room temperature and stirred for 6 hr. The mixture generated precipitates. Solid was filtered and filtrate purified by column chromatography (silica gel 3.5×12 cm with eluent 5% TEA in MeOH/CHCl$_2$=3/7). The yield of combined product of compound 3 was 900 mg (90%) as a white solid. mp: >300° C. (during the test, the color of compound 3 turned to brown at 210° C.). $^1$H NMR (CD$_3$OD, 400 MHz) δ 1.22 (t, 2H), 1.30 (m, 3H), 3.64 (m, 2H), 3.97 (m, 1H), 4.12 (dd, J=11.8 Hz, J=6.4 Hz, 1H), 4.29 (dd, J=11.8 Hz, J=3.6 Hz, 1H), 5.56 (s, 2H), 7.87 (s, 1H), $^{13}$C NMR δ 15.2, 30.7, 35.5, 61.9, 62.6, 66.1, 72.7, 78.1, 117.5, 139.8, 153.3, 155.7, 159.4, 172.2. ESI-MS: m/z 339.1 [M+H]$^+$. HRMS (ESI) cald for C13H19N6O5 [M+H]$^+$ m/z, 339.1417. found 339.1423.

Example 4

1-Methylamino-cyclopropanecarboxylic acid 2-(2-amino-6-oxo-6-dihydro-purin-9-ylmethoxy)-3-hydroxypropyl ester (Compound 4)

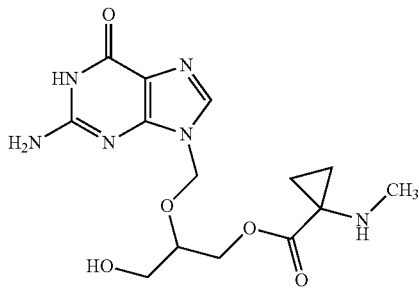 [SMILES: CNC1(C(=O)OCC(CO)OCn2cnc3c(=O)[nH]c(N)nc32)CC1]

Compound 4 was synthesized using a method similar to that described in Examples 2 and 3. Yield (YD): 63%. $^1$H NMR (CD$_3$OD, 400 MHz) δ 1.24 (t, 2H), 1.52 (m, 3H), 2.52 (s, 3H), 3.64 (m, 2H), 3.97 (m, 1H), 4.10 (dd, J=11.8 Hz, J=6.4 Hz, 1H), 4.31 (dd, J=10.2 Hz, J=3.6 Hz, 1H), 5.54 (s, 2H), 7.85 (s, 1H), $^{13}$C NMR δ 12.1, 31.7, 42.5, 62.1, 62.8, 66.3, 72.7, 78.3, 117.5, 139.8, 153.2, 155.9, 159.4, 172.6. ESI-MS: m/z 353.2[M+H]$^+$. HRMS (ESI) cald for C14H21N6O5 [M+H]$^+$ m/z, 339.1573. found 339.1563.

Example 5

1-Amino-2-(4-bromo-phenyl)-cyclopropanecarboxylic acid 2-(2-amino-6-oxo-1,6-dihydro-purin-9-ylmethoxy)-3-hydroxypropyl ester (Compound 5)

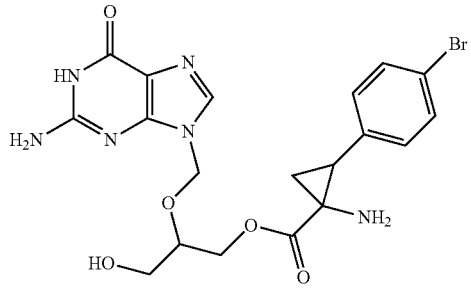 [SMILES: Nc1nc2c(ncn2COC(CO)COC(=O)C2(N)CC2c2ccc(Br)cc2)c(=O)[nH]1]

Compound 5 was synthesized using a method similar to that described in Examples 2 and 3. YD: 30%. $^1$H NMR (CD$_3$OD, 400 MHz) $^1$H NMR (CD$_3$OD, 400 MHz) δ 1.98 (m, 2H), 2.12 (m, 2H), 3.31 (m, 1H), 3.64 (m, 2H), 3.97 (m, 1H), 4.12 (dd, J=11.8 Hz, J=6.4 Hz, 1H), 4.29 (dd, J=11.8 Hz, J=3.6 Hz, 1H), 5.56 (s, 2H), 7.22-7.35 (m, 4H), 7.87 (s, 1H), $^{13}$C NMR δ 17.0, 30.4, 39.5, 61.9, 62.6, 65.7, 72.7, 78.7, 117.5, 119.1, 130.1, 131.2, 136.7, 139.8, 153.3, 155.7, 159.4, 172.2. ESI-MS: m/z 515.1 [M+Na]$^+$.

Example 6

1-Amino-2-phenyl-cyclopropanecarboxylic acid 2-(2-amino-6-oxo-1,6-dihydro-purin-9-ylmethoxy)-3-hydroxypropyl ester (Compound 6)

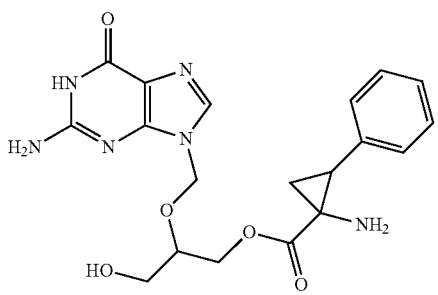

Compound 6 was synthesized using a method similar to that described in Examples 2 and 3. YD: 43%. $^1$H NMR (CD$_3$OD, 400 MHz) $^1$H NMR (CD$_3$OD, 400 MHz) δ 1.98 (m, 2H), 2.12 (m, 2H), 3.33 (m, 1H), 3.64 (m, 2H), 3.92 (m, 1H), 4.10 (dd, J=10.8 Hz, J=6.2 Hz, 1H), 4.32 (dd, J=10.6 Hz, J=3.2 Hz, 1H), 5.53 (s, 2H), 7.36-7.45 (m, 5H), 7.86 (s, 1H), $^{13}$C NMR δ 17.1, 17.4, 30.1, 31.0, 39.2, 40.0, 61.9, 62.6, 65.7, 72.6, 78.7, 117.5, 125.4, 128.1, 129.2, 137.8, 139.8, 153.3, 155.7, 160.1, 172.0, 172.2. ESI-MS: m/z 415.2[M+H]$^+$. HRMS (ESI) cald for C19H23N6O5 [M+H]$^+$ m/z, 415.1730. found 415.1726.

Example 7

Preparation of 1-Amino-2,2-dimethyl-cyclopropanecarboxylic acid 2-(2-amino-6-oxo-1,6-dihydro-purin-9-ylmethoxy)-3-hydroxypropyl ester (Compound 7)

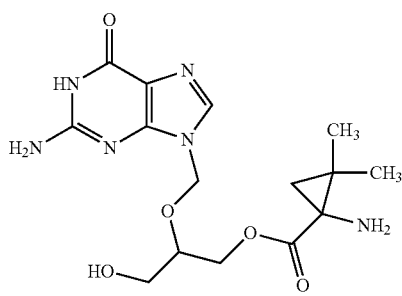 [SMILES: CC1(C)CC1(N)C(=O)OCC(CO)OCn1cnc2c(=O)[nH]c(N)nc21]

Compound 7 was synthesized using a method similar to that described in Examples 2 and 3. YD: 68%, mp=>300° C. H NMR (CD$_3$OD, 400 MHz) δ 1.28 (s, 3H), 1.30 (d, J=6.9, 1H), 1.33 (s, 3H), 1.63 (d, J=6.9, 1H), 3.62 (m, 2H), 3.97 (m, 1H), 4.08 (dd, J=11.6 Hz, J=6.4 Hz, 1H), 4.30 (dd, J=11.6 Hz, J=3.6 Hz, 1H), 5.56 (s, 2H), 7.87 (s, 1H), $^{13}$C NMR δ 15.2, 19.1, 20.2, 25.2, 26.4, 42.4, 61.9, 62.6, 66.1, 72.5, 78.1, 117.5, 140.1, 153.5, 155.7, 160.1, 171.6. ESI-MS: m/z 367.3 [M+H]⁺. HRMS (ESI) cald for C15H23N6O5 [M+H]⁺ m/z, 367.1730. found 367.1732.

Example 8

1-Amino-2-methyl-cyclopropanecarboxylic acid 2-(2-amino-6-oxo-1,6-dihydro-purin-9-ylmethoxy)-3-hydroxypropyl ester (Compound 8)

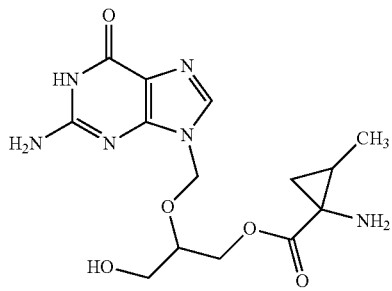

Compound 8 was synthesized using a method similar to that described in Examples 2 and 3, YD: 73%. ¹H NMR (CD₃OD, 400 MHz) δ 0.75-0.85 (m, H1H), 0.99 (m, 2H), 1.24 (d, J=6.8 Hz, 1.5H), 1.52 (m, 0.5H), 1.57 (m, 0.5H), 1.80 (m, 1H), 3.64 (m, 2H), 3.97 (m, 1H), 4.12 (dd, J=11.8 Hz, J=6.4 Hz, 1H), 4.29 (dd, J=11.8 Hz, J=3.6 Hz, 1H), 5.56 (s, 2H), 7.87 (s, 1H). ESI-MS: m/z 353.2 [M+H]⁺.

Example 9

1-Amino-2-trifluoromethyl-cyclopropanecarboxylic acid 2-(2-amino-6-oxo-1,6-dihydro-purin-9-yl-methoxy)-3-hydroxypropyl ester (Compound 9)

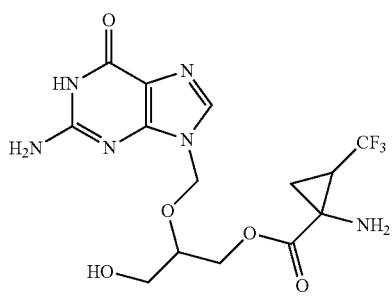

Compound 9 was synthesized using a method similar to that described in Examples 2 and 3, YD: 35%. ¹H NMR (CD₃OD, 400 MHz) 1.83 (m, 1H), 1.94 (m, 1H), 2.80 (m, 1H), 3.62 (m, 2H), 3.95 (m, 1H), 4.12 (dd. J=11.6 Hz, J=6.2 Hz, 1H), 4.27 (dd, J=11.8 Hz, J=3.6 Hz, 1H), 5.59 (s, 2H), 7.85 (s, 1H). ESI-MS: m/z 407.1 [M+H]⁺.

Example 10

1-Amino-2-furan-2-yl-cyclopropanecarboxylic acid 2-(2-amino-6-oxo-1,6-dihydro-purin-9-ylmethoxy)-3-hydroxypropyl ester (Compound 10)

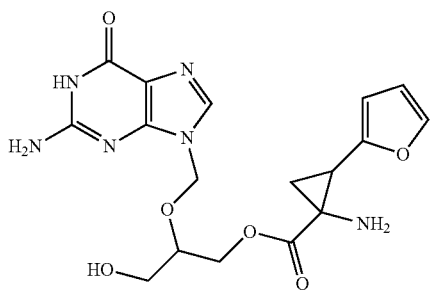 [SMILES: Nc1nc2c(ncn2COC(CO)COC(=O)C2(N)CC2c2ccco2)c(=O)[nH]1]

Compound 10 was synthesized using a method similar to that described in Examples 2 and 3. YD: 30%. ¹H NMR (CD₃OD, 400 MHz) ¹H NMR (CD₃OD, 400 MHz) δ 1.79 (m, 1H), 1.98 (m, 1H), 2.12 (m, 2H), 2.91 (m, 1H), 3.33 (m, 1H), 3.64 (m, 2H), 3.92 (m, 1H), 4.06 (dd, J=9.6 Hz, J=4.2 Hz, 1H), 4.23 (dd. J=9.4 Hz, J=3.2 Hz, 1H), 5.53 (s, 2H), 6.25-6.26 (m, 1H), 6.35-6.36 (m, 1H), 7.34-7.36 (m, 1H) 7.86 (s, 1H). ¹³C NMR δ 16.0, 17.3, 30.3, 31.4, 39.2, 40.4, 61.9, 62.6, 65.7, 72.6, 78.7, 108.4, 110.9, 128.1, 137.8, 142.3, 148.9, 153.3, 155.7, 160.1, 172.0, 172.1. HRMS (ESI) cald for C17H21N6O6 [M+H]⁺ m/z, 405.1523. found 405.1517.

Example 11

1-Amino-2-pyridin-2-yl-cyclopropanecarboxylic acid 2-(2-amino-6-oxo-1,6-dihydro-purin-9-yl-methoxy)-3-hydroxypropyl ester (Compound 11)

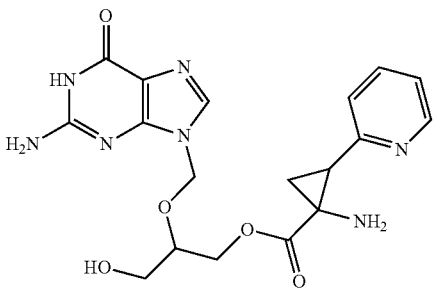

Compound 11 was synthesized using a method similar to that described in Examples 2 and 3. YD: 16%. ¹H NMR (CD₃OD, 400 MHz) ¹H NMR (CD₃OD, 400 MHz) δ 2.01 (m, 1H), 2.15 (m, 1H), 2.12 (m, 2H), 3.14 (m, 1H), 3.33 (m, 1H), 3.64 (m, 2H), 3.93 (m, 1H), 4.12 (dd, J=9.4 Hz, J=4.2 Hz, 1H), 4.25 (dd, J=9.2 Hz, J=3.2 Hz, 1H), 5.57 (s, 2H), 7.32-7.37 (m, 1H), 7.46-7.49 (m, 1H), 7.77-7.83 (m, 1H), 7.86 (s, 1H), 8.60-8.64 (m, 1H). ¹³C NMR δ 16.7, 17.1, 30.6, 31.48, 39.3, 40.8, 61.7, 62.6, 66.1, 72.8, 78.8, 108.4, 110.9, 128.1, 137.8, 142.3, 148.9, 152.3, 155.6, 160.1, 173.0, 173.2.

Example 12

Hydrolytic Stability of Compound 3 and Analogues Thereof

Compound 3 and its analogues (substituted 1-Amino-cyclopropanecarboxylic acid 2-(2-amino-6-oxo-1,6-dihydro-purin-9-yl methoxy)-3-hydroxypropyl esters) were tested for hydrolytic stability in a phosphate-buffered solution of various pH (1, 4, 7.4, 10) at a concentration of 1 mg/mL and 40° C., using a semi-automated HPLC technique during the period of 12 h. Hydrochloric acid of 0.1 N was used for pH 1 solution.

Samples were repeatedly, manually injected onto HPLC at specific time intervals at room temperature. The peak areas of the compounds were monitored by UV detection. Compound 3 was stable in an acidic solution (pH 4) with $T_{1/2}$>300 hrs. In the physiological conditions (pH=7.4), its half life value ($T_{1/2}$) was 53 hrs (FIG. 1). The half life value ($T_{1/2}$, at pH 7.4, 40° C.) of its analogues, Compound 5, 6, 7, 8, 9, 10, 11 were 85, 75, 68, 58, 33, 29, 43 hrs, respectively. The "half life value, $T_{1/2}$," means the time required for one-half of the total amount of a compound in a solution to be degraded by hydrolysis processes when the rate of removal is nearly exponential. The half-life was calculated as follows: The peak area of the compound sample was monitored in a 12-hour period at 2 hour intervals, and plotted versus lime for each of the buffers tested. A first order calculation was used to determine the rate constant for each buffer on the loss of peak area over time.

Example 13

Aqueous Solubility of Compound 3 and Analogues Thereof

The solubility of Compound 3 and its analogues (substituted 1-Amino-cyclopropanecarboxylic acid 2-(2-amino-6-oxo-1,6-dihydro-purin-9-yl methoxy)-3-hydroxypropyl esters) were analyzed.

The solubility experiment procedure was modified due to chemical stabilities. Briefly, an excess of a test compound was added 0.5 mL of water in an one mL of vial, pre-equilibrated, and then sonicated at 23° C. for 3 min. Aliquots were filtered and analyzed for drug contents. The concentration of each compound was determined by HPCL, at λ=254 nm, 23° C. The aliquot containing the analyte was diluted 100× due to the detection limit of the instrument. The results showed that the aqueous solubility of Compound 3 was 180 mg/ml, which was superior to ganciclovir (solubility 2.6 mg/ml). The solubility of compounds 4, 5, 6, 7, 9, 10, 11 were 227, 155, 170, 213, 261, 260, 253 mg/ml, respectively.

Example 14

In vitro Anti-HSV activity of 1-Amino-cyclopropanecarboxylic acid 2-(2-amino-6-oxo-1,6-dihydro-purin-9-yl methoxy)-3-hydroxypropyl ester (Compound 3)

Human epithelial (HEp-2) cells were cultured in MEM supplemented with 10% fetal calf serum and 10% heat activated newborn calf serum. Vero cells were cultured in RPMI-1640 and 10% heat activated newborn calf serum. Penicillin (1000 I.U./ml), streptomycin (100 μg/ml), and bicarbonate buffer were present in the medium, and cells were maintained at 37° C., 5% CO2, humidified atmosphere, and subcultured 2~3 times a week.

Figure 2:
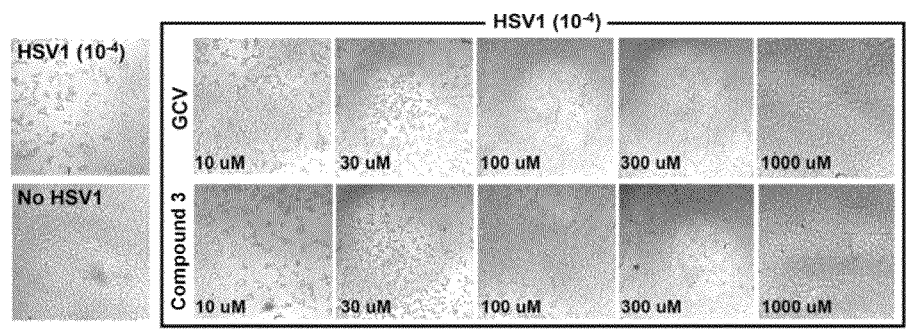
FIG. 2 shows the results of morphological evaluation of the effect of Compound 3 on the cytopathogenic effect of HSV-1 on Vero cells. Inoculation of HSV-1 on Vero cells triggered cytopathogenic effects (left-upper panel). The morphology of Vero cells without HSV-1 inoculation was shown in left-bottom panel. The HSV-1- (at $10^{-4}$ titration) inoculated Vero cell were treated with ganciclovir (GCV) or Compound 3 of different concentrations for 4 days. Compound 3 reduced the cytopathogenic effects of HSV-1 on Vero cells in a concentration-dependent manner.

The antiviral activity of Compound 3 was determined by evaluating the attenuation in HSV-1 induced cytopathic effects on Vero cells. Vero cells (10,000 cells/well) in a 96-well culture plate were infected with an increasingly diluted HSV-1 virus solution ($10^{-3}$ to $10^{-5}$) in L15 medium. After 2 h incubation the unadsorbed virus was removed, the cell monolayer was washed with PBS. Then, different concentrations of Compound 3 and ganciclovir, both of which having been identified as nontoxic to Vero cells, were added and further incubated at 37° C. for 7 days. Every 24 hr the cytopathic effects were observed and photographed under microscope (FIG. 2). Anti-HSV-1 activity was determined by inhibition of cytopathic effect as compared with control. The cytopathic effects effects after HSV-1 propagation HSV-1 between Vero cells were quantified in terms of 50% tissue culture infective dose (TCID50, which was used to determine the infectious titer of HSV-1 which can cause cytopathic effects in culture).

Example 15

In vivo anti-HSV activity of 1-Amino-cyclopropanecarboxylic acid 2-(2-amino-6-oxo-1,6-dihydro-purin-9-yl methoxy)-3-hydroxypropyl ester (Compound 3)

The effect of Compound 3 on herpetic keratitis was investigated in mice with cornea inoculated by HSV-1. Balb/c mice (eight weeks old, 25 g body weight) were anesthetized with isoflurane, and epithelium of both right and left corneas lightly scratched in a cross-hatch pattern (four horizontal and four vertical scratches) with a 26-gauge needle under a microscope. The mouse cornea was inoculated with 5 μL of HSV-1 suspension containing $2.5 \times 10^6$ plaque-forming units (PFU), or saline for control. After the inoculations, mice were assigned randomly to treatment groups (4~5 mice per group), with both eyes treated with Compound 3 or ganciclovir or vehicle (saline) after lightly anaesthetized. Eight hours after HSV-1 inoculation, 1 drop (10 μl) of 0.34% or 0.2% w/v solution of compound 3 or ganciclovir in saline with antifungi agent (0.05 w/v amphotericin-B) was applied to each eye daily, 3 times a day. The keratitis was graded, recorded and scored daily for 21 days, and the eyes were examined with a microscopic camera at frequent intervals.

Figure 3:
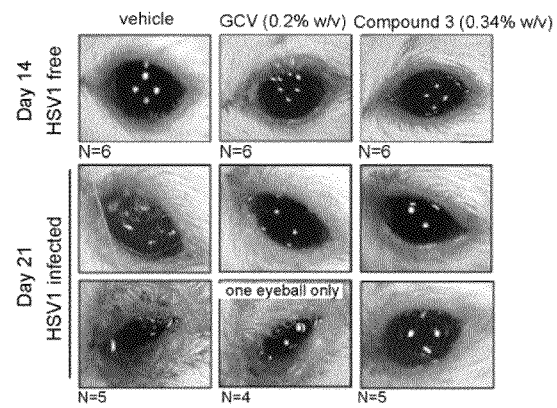
FIG. 3 shows reduction in keratitis by local delivery of compound 3 on HSV-1-inoculated mice. Mice were each inoculated with HSV-1 and treated with eye-drops containing compound 3 or ganciclovir (GCV) in saline three times a day. The effects of Compound 3 and GCV on the development of corneal clouding and keratitis were recorded, scored and photographed by a microscopic camera. The vehicle was saline only.

On day-14, corneal cloudiness were found in the vehicle-treated group, and were much more significant than ganciclovir (GCV)- or Compound 3-treated group. On day-21, the severity of the ocular disease symptoms such as corneal clouding, stromal keratitia and blephartitis (ulcer extending beyond the eyelids) increased in the vehicle-treated group. The ganciclovir treatment reduced the severities in stromal keratitia and corneal clouding dramatically, but blephartitis still existed. Compound 3, after long term ocular delivery, eliminated the extra-ocular keratitis morphologies almost entirely (FIG. 3).

Example 16

Pharmacokinetic studies of 1-Amino-cyclopropanecarboxylic acid 2-(2-amino-6-oxo-1,6-dihydro-purin-9-yl methoxy)-3-hydroxypropyl ester (Compound 3)

Oral absorption of Compound 3 was studied at a dose of 34 mg/kg. Male SD rats (250-300 g) were used. Animals were fasted overnight (12-18 h) with a free access to water. Freshly prepared compound solution in DI water was administrated by oral gavage (1 mL). Blood samples (200 μL) were collected from tail veins at 0.5, 1, 1.5, 2, 2.5, 3, 5, 16 h. Similar experiments were carried out at a dose of 26.5 mg/kg with male balb-c mice (20-25 g), except that 0.2 mL of freshly prepared compound solution was administrated. Blood samples (200 μL) were collected from hearts at 0, 20, 40, 60, 80, 100, 120, 140, 160, 180, 220, 300, 480 min.

Figure 4:
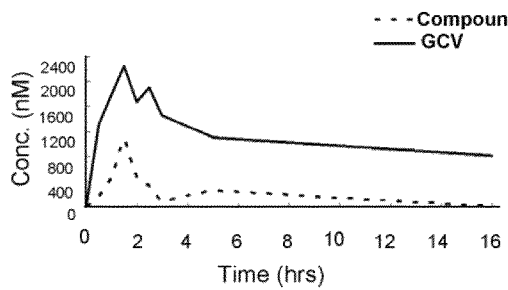
FIGS. 4-5 are plasma concentration curves of Compound 3 (dash line, ester or prodrug form) and its metabolite (solid line, hydrolysis product, ganciclovir (GCV), showing plasma drug concentration vs time after an oral dose of Compound 3 in rat (25 mg/kg) and mice (26.5 mg/kg), respectively.
Figure 5:
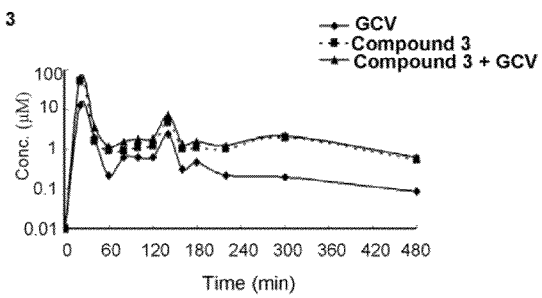

Comparing to ganciclovir (GCV), the bioavailability of Compound 3 is better than ganciclovir. FIGS. 4-5 show the plasma concentrations of Compound 3 (dash line) and its metabolite ganciclovir (GCV; solid line) at various time points in rat (FIG. 4) or mice (FIG. 5) after drug administration using HPLC analysis (n≥5).

A compound of Formula (T):

Formula (T)

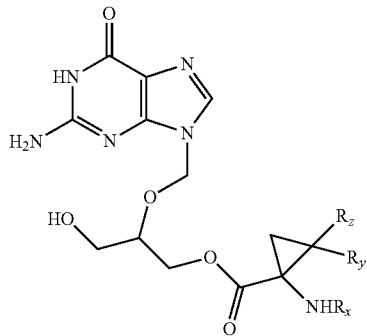

TABLE I

| Compound Number | Chemical Name | Structure | Substituents of Formula (T) |
|---|---|---|---|
| Cpd. 3 | 1-Amino-cyclopropanecarboxylic acid 2-(2-amino-6-oxo-1,6-dihydro-purin-9-yl methoxy)-3-hydroxy propyl ester | 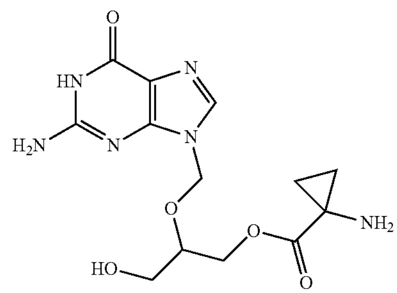 [SMILES: Nc1nc2c(ncn2COC(CO)COC(=O)C2(N)CC2)c(=O)[nH]1] | $R_x$ = hydrogen<br>$R_y$ = hydrogen<br>$R_z$ = hydrogen |
| Cpd. 4 | 1-Methylamino-cyclopropanecarboxylic acid 2-(2-amino-6-oxo-1,6 dihydro-purin-9-ylmethoxy)-3-hydroxypropyl ester | 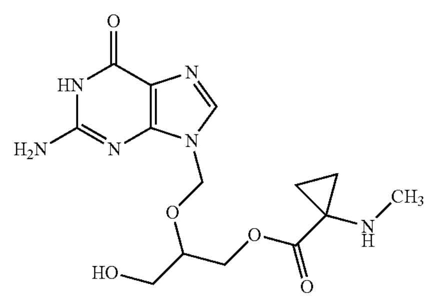 [SMILES: CNC1(C(=O)OCC(CO)OCn2cnc3c(=O)[nH]c(N)nc32)CC1] | $R_x$ = methyl<br>$R_y$ = hydrogen<br>$R_z$ = hydrogen |
| Cpd 5 | 1-Amino-2-(4-bromo-phenyl)-cyclopropanecarboxylic acid 2-(2-amino-6-oxo-1,6-dihydro-purin-9-ylmethoxy)-3-hydroxypropyl ester | 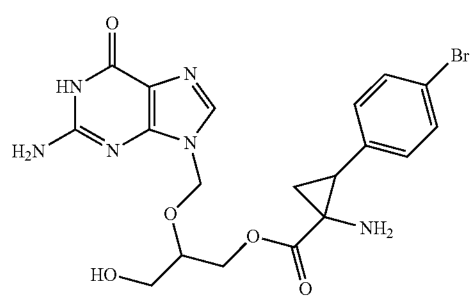 [SMILES: Nc1nc2c(ncn2COC(CO)COC(=O)C2(N)CC2c2ccc(Br)cc2)c(=O)[nH]1] | $R_x$ = hydrogen<br>$R_y$ = 4-bromophenyl<br>$R_z$ = hydrogen |
| Cpd. 6 | 1-Amino-2-phenyl-cyclopropanecarboxylic acid 2-(2-amino-6-oxo-1,6-dihydro-purin-9-ylmethoxy)-3-hydroxypropyl ester | 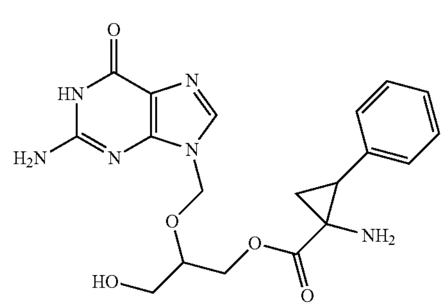 | $R_x$ = hydrogen<br>$R_y$ = phenyl<br>$R_z$ = hydrogen |

TABLE I-continued

| Compound Number | Chemical Name | Structure | Substituents of Formula (T) |
|---|---|---|---|
| Cpd. 7 | 1-Amino-2,2-dimethyl-cyclopropanecarboxylic acid 2-(2-amino-6-oxo-1,6-dihydro-purin-9-ylmethoxy)-3-hydroxypropyl ester | 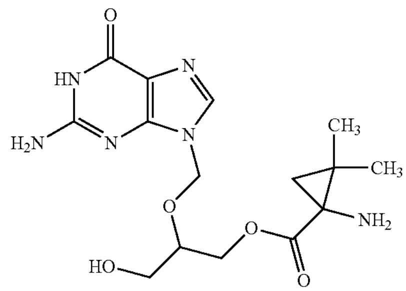 [SMILES: CC1(C)CC1(N)C(=O)OCC(CO)OCn1cnc2c(=O)[nH]c(N)nc21] | $R_x$ = hydrogen<br>$R_y$ = methyl<br>$R_z$ = methyl |
| Cpd. 8 | 1-Amino-2-methyl-cyclopropanecarboxylic acid 2-(2-amino-6-oxo-dihydro-purin-9-ylmethoxy)-3-hydroxypropyl ester | 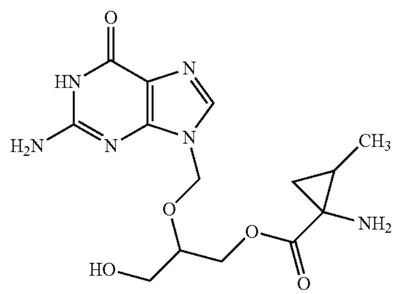 | $R_x$ = hydrogen<br>$R_y$ = methyl<br>$R_z$ = hydrogen |
| Cpd. 9 | 1-Amino-2-trifluoromethyl-cyclopropanecarboxylic acid 2-(2-amino-6-oxo-1,6-dihydro-purin-9-ylmethoxy)-3-hydroxypropyl ester | 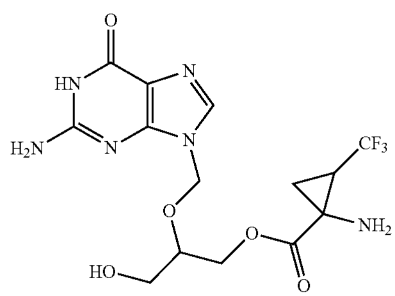 | $R_x$ = hydrogen<br>$R_y$ = trifluoromethyl<br>$R_z$ = hydrogen |
| Cpd. 10 | 1-Amino-2-furan-2-yl-cyclopropanecarboxylic acid 2-(2-amino-6-oxo-1,6-dihydro-purin-9-ylmethoxy)-3-hydroxypropyl ester | 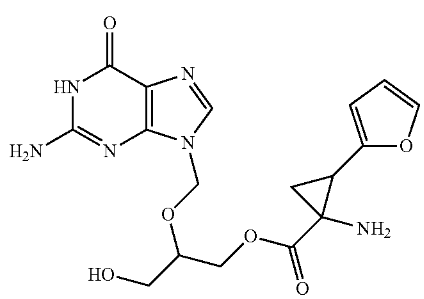 [SMILES: Nc1nc2c(ncn2COC(CO)COC(=O)C2(N)CC2c2ccco2)c(=O)[nH]1] | $R_x$ = hydrogen<br>$R_y$ = 2-furyl<br>$R_z$ = hydrogen |
| Cpd. 11 | 1-Amino-2-pyridin-2-yl-cyclopropanecarboxylic acid 2-(2-amino-6-oxo-1,6-dihydro-purin-9-ylmethoxy)-3-hydroxypropyl ester | 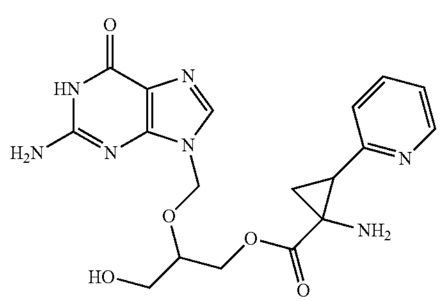 [SMILES: Nc1nc2c(ncn2COC(CO)COC(=O)C2(N)CC2c2ccccn2)c(=O)[nH]1] | $R_x$ = hydrogen<br>$R_y$ = 2-pyridyl<br>$R_z$ = hydrogen |

$R_x$ and $R_z$ are each independently hydrogen or methyl; and
$R_y$ is hydrogen, methyl, trifluoromethyl, phenyl, 4-bromophenyl, 2-furyl, or 2-pyridyl.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

All references cited and discussed in this specification are incorporated herein by reference in their entireties and to the same extent as if each reference was individually incorporated by reference.

What is claimed is:

1. A compound having the structure

Formula (T)

or a pharmaceutically acceptable salt thereof, wherein
  $R_x$ and $R_z$ are each independently hydrogen or $(C_1-C_6)$ alkyl; and
  $R_y$ is $(C_1-C_6)$alkyl, halo$(C_1-C_6)$alkyl, $(C_6-C_{18})$aryl, halo$(C_6-C_{18})$aryl, or $(C_3-C_{18})$heteroaryl.

2. The compound of claim 1, wherein
  $R_x$, and $R_z$, are each independently hydrogen or methyl; and
  $R_y$ is methyl, trifluoromethyl, phenyl, 4-bromophenyl, 2-furyl, or 2-pyridyl.

3. The compound of claim 2, wherein
  $R_x$, and $R_z$, are each independently hydrogen; and
  $R_y$ is methyl, trifluoromethyl, phenyl, 4-bromophenyl, 2-furyl, or 2-pyridyl.

4. The compound of claim 2, wherein
  $R_x$ is methyl; and
  $R_z$ is hydrogen.

5. The compound of claim 2, wherein the compound is selected from the group consisting of
  1-amino-2-(4-bromo-phenyl)-cyclopropanecarboxylic acid 2-(2-amino-6-oxo-1,6-dihydro-purin-9-yl-methoxy)-3-hydroxypropyl ester,
  1-amino-2-phenyl-cyclopropanecarboxylic acid 2-(2-amino-6-oxo-1,6-dihydro-purin-9-ylmethoxy)-3-hydroxypropyl ester,
  1-Amino-2,2-dimethyl-cyclopropanecarboxylic acid 2-(2-amino-6-oxo-1,6-dihydro-purin-9-ylmethoxy)-3-hydroxypropyl ester,
  1-amino-2-methyl-cyclopropanecarboxylic acid 2-(2-amino-6-oxo-1,6-dihydro-purin-9-ylmethoxy)-3-hydroxypropyl ester,
  1-amino-2-trifluoromethyl-cyclopropanecarboxylic acid 2-(2-amino-6-oxo-1,6-dihydro-purin-9-ylmethoxy)-3-hydroxypropyl ester,
  1-amino-2-furan-2-yl-cyclopropanecarboxylic acid 2-(2-amino-6-oxo-1,6-dihydro-purin-9-ylmethoxy)-3-hydroxypropyl ester, and
  1-amino-2-pyridin-2-yl-cyclopropanecarboxylic acid 2-(2-amino-6-oxo-1,6-dihydro-purin-9-yl-methoxy)-3-hydroxypropyl ester.

6. A composition comprising the compound of claim 1, or a pharmaceutically acceptable salt thereof, and a pharmaceutically acceptable carrier or vehicle.

7. A method for preparing a compound as claimed in claim 1, comprising the steps of:
  (1) reacting a compound of Formula (W)

Formula (W)

with a mixture of dimethylforamide/dimethylacetamide to afford a compound of Formula (X)

Formula (X)

(2) reacting the compound of Formula (X) with a compound of Formula (Y)

Formula (Y)

wherein $R_x$ and $R_z$ are each independently hydrogen or $(C_1-C_6)$alkyl; and $R_y$ is $(C_1-C_6)$alkyl, halo$(C_1-C_6)$alkyl, $(C_6-C_{18})$aryl, halo$(C_6-C_{18})$aryl, or $(C_3-C_{18})$heteroaryl to afford a compound of Formula (Z)

Formula (Z)

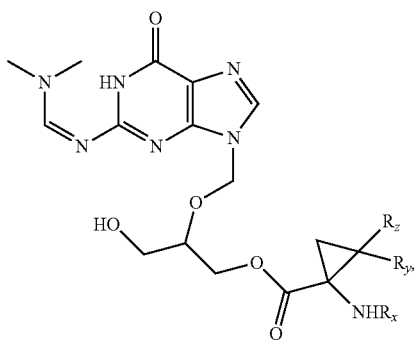

wherein $R_x$ and $R_z$ are each independently hydrogen or ($C_1$-$C_6$)alkyl; and $R_y$ is ($C_1$-$C_6$)alkyl, halo($C_1$-$C_6$)alkyl, ($C_6$-$C_{18}$) aryl, halo($C_6$-$C_{18}$)aryl, or ($C_3$-$C_{18}$)heteroaryl; and (3) reacting the compound of Formula (Z) with methanol and trifluoroacetic acid to afford the compound of Formula (T), wherein $R_x$ and $R_z$ are each independently hydrogen or ($C_1$-$C_6$)alkyl; and $R_y$ is ($C_1$-$C_6$)alkyl, halo ($C_1$-$C_6$)alkyl, ($C_6$-$C_{18}$)aryl, halo($C_6$-$C_{18}$)aryl, or ($C_3$-$C_{18}$)heteroaryl.

8. A method of treating herpes virus infection, comprising administering to a subject in need thereof the compound of claim 1, or a pharmaceutically acceptable salt thereof.

9. The method of claim 8, wherein the herpes virus infection is at least one selected from the group consisting of herpes simplex virus infection, herpes zoster infection, or cytomegalovirus infection.

10. A method of treating herpes virus infection, comprising administering to a subject in need thereof the compound of claim 2, or a pharmaceutically acceptable salt thereof.

11. A method of treating herpes virus infection, comprising administering to a subject in need thereof the compound of claim 3, or a pharmaceutically acceptable salt thereof.

12. A method of treating herpes virus infection, comprising administering to a subject in need thereof the compound of claim 4, or a pharmaceutically acceptable salt thereof.

13. A compound having the structure

Formula (T)

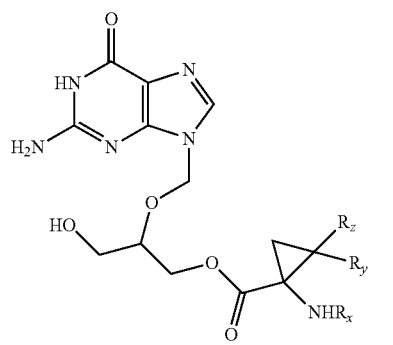

or a pharmaceutically acceptable salt thereof, wherein $R_x$ is ($C_1$-$C_6$)alkyl; and $R_y$ is hydrogen, ($C_1$-$C_6$)alkyl, halo($C_1$-$C_6$)alkyl, ($C_6$-$C_{18}$) aryl, halo($C_6$-$C_{18}$)aryl, or ($C_3$-$C_{18}$)heteroaryl; and $R_z$ is hydrogen or ($C_1$-$C_6$)alkyl.

14. The compound of claim 13, wherein $R_x$ is methyl;

$R_y$ is hydrogen, methyl, trifluoromethyl, phenyl, 4-bromophenyl, 2-furyl, or 2-pyridyl; and $R_z$ is hydrogen.

15. The compound of claim 14, wherein $R_x$ is methyl; and $R_y$ and $R_z$ are each independently hydrogen.

16. A method for preparing a compound as claimed in claim 13, comprising the steps of:

(1) reacting a compound of Formula (W)

Formula (W)

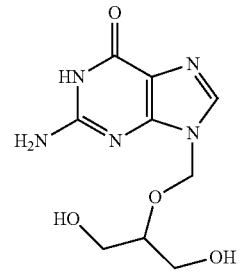

with a mixture of dimethylforamide/dimethylacetamide to afford a compound of Formula (X)

Formula (X)

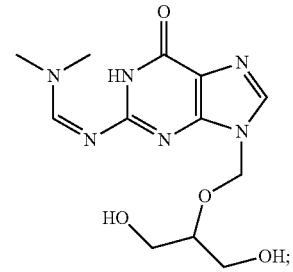

(2) reacting the compound of Formula (X) with a compound of Formula (Y)

Formula (Y)

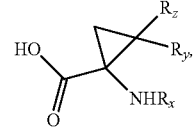

wherein $R_x$ is ($C_1$-$C_6$)alkyl; $R_y$ is hydrogen, ($C_1$-$C_6$)alkyl, halo($C_1$-$C_6$)alkyl, ($C_6$-$C_{18}$)aryl, halo($C_6$-$C_{18}$)aryl, or ($C_3$-$C_{18}$)heteroaryl; and $R_z$ is hydrogen or ($C_1$-$C_6$)alkyl, to afford a compound of Formula (Z)

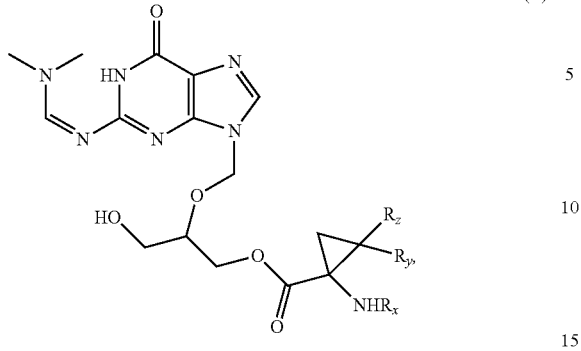

Formula (Z)

wherein $R_x$ is $(C_1\text{-}C_6)$alkyl; $R_y$ is hydrogen, $(C_1\text{-}C_6)$alkyl, halo$(C_1\text{-}C_6)$alkyl, $(C_6\text{-}C_{18})$aryl, halo$(C_6\text{-}C_{18})$aryl, or $(C_3\text{-}C_{18})$heteroaryl; and $R_z$ is hydrogen or $(C_1\text{-}C_6)$alkyl; and (3) reacting the compound of Formula (Z) with methanol and trifluoroacetic acid to afford the compound of Formula (T), wherein $R_x$ is $(C_1\text{-}C_6)$alkyl; $R_y$ is hydrogen, $(C_1\text{-}C_6)$alkyl, halo$(C_1\text{-}C_6)$alkyl, $(C_6\text{-}C_{18})$aryl, halo$(C_6\text{-}C_{18})$aryl, or $(C_3\text{-}C_{18})$heteroaryl; and $R_z$ is hydrogen or $(C_1\text{-}C_6)$alkyl.

17. A composition comprising the compound of claim 13, or a pharmaceutically acceptable salt thereof, and a pharmaceutically acceptable carrier or vehicle.

18. A method of treating herpes virus infection, comprising administering to a subject in need thereof the compound of claim 13, or a pharmaceutically acceptable salt thereof.

* * * * *